United States Patent [19]

Lundbäck

[11] Patent Number: 4,648,877
[45] Date of Patent: Mar. 10, 1987

[54] BLOOD PUMP

[75] Inventor: Stig Lundbäck, Vaxholm, Sweden

[73] Assignee: Astra-Tech Aktiebolag, Stockholm, Sweden

[21] Appl. No.: 709,557

[22] Filed: Apr. 26, 1985

[30] Foreign Application Priority Data

Mar. 30, 1984 [SE] Sweden .............................. 8401778

[51] Int. Cl.[4] .............................................. A61F 2/22
[52] U.S. Cl. ...................................................... 623/3
[58] Field of Search ..................... 623/3; 417/412, 413, 417/472, 473

[56] References Cited

U.S. PATENT DOCUMENTS 3,097,366  7/1963  Winchell ................................. 623/3
3,656,873  4/1972  Schiff ..................................... 623/3

FOREIGN PATENT DOCUMENTS 844815  7/1981  U.S.S.R. ................................ 623/3

OTHER PUBLICATIONS

"Cardiac Pumping and Function of the Ventricular Septum", by Stig Condback, Karolinska Institute, 1986.

Primary Examiner—Richard J. Apley
Assistant Examiner—James Prizant
Attorney, Agent, or Firm—Brumbaugh, Graves, Donohue & Raymond

[57] ABSTRACT

A blood pump comprises an atrium chamber defined by flexible walls and having an inlet and an outlet, a ventricle chamber defined by flexible walls and having an inlet and an outlet, a passage communicating the outlet of the atrium chamber with the inlet of the ventricle chamber, a first one-way valve in the passage adapted to permit blood flow only from the atrium chamber to the ventricle chamber, and a second one-way valve in the outlet from the ventricle chamber adapted to permit blood to flow through the outlet only out of the ventricle chamber. The chambers are movably supported in a casing having first and second openings, the atrium chamber inlet being fastened to the first opening and the ventricle chamber outlet to the second opening. A drive device cyclically moves the walls of the ventricle chamber to decrease its volume and expel blood from it while simultaneously moving the walls of the atrium chamber such that its volume may increase upon inflow of blood into the inlet to it. The drive device includes a drive ring surrounding and joined to the passage and having a surface engageable with the walls of the ventricle chamber over a selected area such that the pressure of blood entering the chambers between driven strokes of the drive device controls the output of the blood pump by establishing the magnitude of the return stroke of the drive ring as a function of a pressure force acting over the area of engagement between the drive ring and the walls of the ventricle chamber.

16 Claims, 8 Drawing Figures

BLOOD PUMP

FIELD OF THE INVENTION

The present invention is a blood pump suitable for either temporary use outside the body (e.g., as part of a heart-lung machine) or as a temporary heart prothesis implanted in the body.

BACKGROUND OF THE INVENTION

U.S. Pat. No. 3,097,366 describes and illustrates a heart pump comprising two elastic bags joined by a one-way valve and contained in a casing. The ventricle bag is periodically squeezed between a driven plate and the casing wall to pump the blood. The ventricle bag is cemented to the driven plate, which is resiliently urged in a direction to expand the ventricle bag between driven pulses for forced refilling. The atrium bag is larger than the ventricle bag so inflow during the pumping stroke can occur because of partial collapse of the atrium bag during each outflow pulse. The only way to regulate this heart pump is to vary the speed of the drive (pulse).

The heart pump of U.S. Pat. No. 3,656,873, which is intended for temporary use in heart surgery, also has two bag-like flexible containers with a one-way valve at the outlet of the bag that serves as the ventricle. Each flexible container is mounted in a separate rigid container so that the outside of such flexible container can be exposed cyclically to pneumatic pressure. The ventricle container is compressed intermittently to give a pulsating flow.

The atrium container is subjected to pressure or vacuum, which determines the intake of blood. To the extent that the pressure of the incoming blood exceeds the pressure outside the atrium container, blood will be taken in. The pressure outside the ventricle container is varied, and blood is admitted from the atrium if the pressure in the ventricle is lower than in the atrium, in which case the one-way valve allows the blood to pass until the pulsation causes the pressure in the ventricle volume to exceed the atrium pressure. It is evident that this design can be regulated by varying the frequency and pressure of the pneumatic pulses, but it cannot be adjusted to a constant setting of the intake velocity because the atrium volume is independent of the volume of the ventricle.

U.S.S.R. (Russian) Pat. No. 944815 (1981) describes and shows a blood pump comprising either a ventricle chamber or both an atrium chamber and ventricle chamber, each of bulbous shape and having a flexible walls, received in a casing. The ventricle chamber is periodically and repeatedly compressed by movement of the armature of a linear electric motor working through a convexly curved annular drive shoe that is connected to a valve plate at the inlet to the ventricle chamber. The return stroke is provided by a spring. The arrangement is such that the intake stroke is strongly influenced by the spring. Hence, the device is essentially a positive displacement pump, the output of which can be varied only by changing the pulse rate.

The present invention has arisen out of the discovery of the present inventor that the human heart does not work in the way it is generally believed to. Because this constitutes part of the background of the invention, a short explanation will be given here in order to make the invention easier to understand. A more detailed description of the inventor's findings is found in Lundback, S. Cardiac Pumping and Function of the Ventricular Septum. Supplementum 550 1986 to Acta Physiologica Scandinavica (ISBN 91-7900-066-5).

Starting from the observation made in, inter alia, ultrasonic examinations that the volume of the heart during a beat often only varies by less than 10%, together with the observation that the incoming blood is not appreciably pulsating and the blood coming out is vigorously pulsating, it has been possible to predict and to clinically ascertain that what happens when the heart is beating is that the heart muscle at contraction is pulling the dividing walls at the atria, including the heart valves, down towards the heart apex. When the heart muscle thereafter relaxes, the plane of the valves will be pressed upwards, not by muscle power but by the dynamic and static forces of the inflowing blood and by elastic components within and outside the heart. Thus the volumes of the ventricles will decrease and the volumes of the atria will increase during the systolic phase, and the sum of these volumes is somewhat decreasing and the outer shape of the heart thus decreases in the systolic phase. More blood than is coming in is thus pumped out during systole. The inflow into the atria, however, continues during systole by enlargement of the atria. During diastole, the valves in the aorta and the pulmonary artery close, and the inflow into the atria continues because the total heart volume is somewhat increasing. The plane of the valves returns upwards, more or less depending on the refilling volume, whereby the displacement volume in the subsequent ventricular systole is determined by the amount of blood flowing into the heart during both systole and diastole. These findings, in conjunction with another discovery concerning the regulating function of the cardiac septum, must be considered a surprise and might induce a true paradigm shift within the sciences concerned.

Moreover, it can now be explained how the heart is filled during diastole, i.e., what power is causing variation in the volume of the heart. The fact is that the heart muscle is constituted in such way that it has a capability of contraction, but after contraction has to be stretched by the aid of another force. According to the inventor's findings, this force is a hydrodynamic impact-type force caused by kinetic energy imparted to the blood in the heart during systole, which at the end of systole and at the closing of aortic and pulmonic valves is transformed to a pressure which has a tendency to increase the ventricular volume by, among other things, pressing the valve plane upwards.

SUMMARY OF THE INVENTION

It is one aim of the invention to provide a self-regulating blood pump which, in conformity with the present inventor's discoveries, produces a pulsating outflow but a substantially constant pressure inflow. Another aim is to provide a pump having an effective displacement volume that varies in dependence upon the filling pressure.

Yet another aim is to provide a pump that is suitable for replacing or supporting the function of the natural heart in vivo. One further aim of the invention is that it be suitable for being driven by an essentially constant force, for example, a paced striated autologous muscle, to provide the heart prosthesis with a power source generated by the body.

To attain the objectives referred to above, there is provided, according to the present invention, a blood pump comprising an atrium chamber defined by flexible walls and having an inlet and an outlet, a ventricle chamber defined by flexible walls and having an inlet and an outlet, a passage communicating the outlet of the atrium chamber with the inlet of the ventricle chamber, a first one-way valve in the passage adapted to permit blood flow only from the atrium chamber to the ventricle chamber, and a second one-way valve in the outlet from the ventricle chamber adapted to permit blood to flow through the outlet only out of the ventricle chamber. The chambers are movably supported in a casing having first and second openings, the atrium chamber inlet being fastened to the first opening and the ventricle chamber outlet to the second opening. A drive device periodically and selectively moves the walls of the ventricle chamber to decrease its volume and expel blood from it while simultaneously moving the walls of the atrium chamber such that its volume may increase upon inflow of blood into the inlet to it. The drive device includes a drive ring surrounding and joined to the passage and having a surface engageable with the walls of the ventricle chamber over a selected area such that the pressure of blood entering the chambers between driven strokes of the drive device controls the output of the blood pump by establishing the magnitude of the return stroke of the drive ring as a function of a pressure force acting over the area of engagement between the drive ring and the walls of the ventricle chamber.

A preferred embodiment of the invention includes the following additional characteristics individually or in combination:

1. The drive device engages the drive ring only during the driven stroke of the pump and disengages from the drive ring and moves to a retracted position during the return stroke of the pump.

2. The casing is hermetically sealed and contains a gas exteriorly of the chambers, the pressure of which varies as a function of the variation of the instantaneous total volume of the chambers and thereby influences the inflow of blood during the return stroke. A pressure control valve controls the pressure of the gas in the casing.

3. The casing and all components of the drive are contained in an enclosure, and the interior of the casing communicates with the enclosure through a pressure control valve.

4. The atrium and ventricle chambers and the passage are portions of a one-piece hose-like member of flexible and substantially nonextensible material.

5. The inlet to the atrium chamber and the outlet from the ventricle chamber are at generally opposite ends of the casing and are also generally opposite the passage across the respective chambers.

6. The chambers and passage are substantially symmetrical rotationally about an axis of symmetry defined by a line joining the inlet to the atrium chamber and the outlet from the ventricle chamber. Likewise, the casing and the drive ring are substantially symmetrical rotationally about an axis of symmetry coincident with the axis of symmetry of the chambers and passage.

7. Portions of the walls of each chamber are engageable during portions of each operating cycle between a surface of the drive ring and an interior wall surface of the casing, and the surfaces engageable with the respective chamber walls are dish-shaped and of generally complementary shapes. Preferably, the surface of the drive ring that engages one of the chambers is convex and the surface of the drive ring that engages the other chamber is concave. The area of the surface of the drive ring that engages the ventricle chamber is substantially greater than the area of the surface of the drive ring that engages the atrium chamber during a substantial part of the return stroke of the pump, whereby the volume of blood taken into the pump between strokes is a function of the dynamic and static forces of the blood entering the chambers during the return stroke.

As mentioned above, it is desirable to make the walls forming the chambers not only flexible but substantially inextensible, e.g., by using reinforced plastics. Also, they should be smooth on the inside to avoid coagulation phenomena and should, of course, be mde of a material that behaves inertly, e.g. silicone rubber or polyurethane.

The invention is a single pump, whereas the anatomical heart is a double pump. However, in many cases it is possible to insert into the blood circulation system, which essentially consists of a closed loop with two different pumps, acting in cooperation, a single pump only. The loop in the circulation systems which goes via pulmonary artery, lungs and pulmonary vein has, of course, a relatively low drop in pressure, compared with the main circulation system, aorta—blood vessels of the body—venous sytem.

Among other things, the possibility to implant a pump according to the invention with the heart remaining in the body is presented, with its inlet tube inserted into the left ventricle and its outlet tube connected to the aorta. By doing this the heart load can be reduced, and there is a possibility of removing the heart prosthesis later on after a healing period for the insufficient heart. Because of the low pressure drop in the lungs, even an insufficient heart will manage the pumping in this part of the circulatory system.

The heart prosthesis is in this case suitably implanted in the abdominal cavity and driven by a linear or rotary electric motor powered by a rechargeable storage battery, which may be charged during the patient's sleep, either through electrodes penetrating the skin or by a transformer-type effect on an implanted receiver coil.

Because of the self-regulation of the displacement volume by the pump, is is also possible, according to the invention, to manufacture a double pumping device performing the functions of both the left and right heart sections. Two devices of the kind mentioned, driven in parallel or separately, may be used for this purpose, the essential requirement being that the amounts pumped per time unit for both pumps be equal.

If two pumps of the type described above are used, which can work in step or out of step and with the same or a different motor, a coupling of the pumps will be achieved via the flow. The self-regulation of the displacement volumes by the pumps, which is a function of the filling pressures, will meet the requirement that the filling pressures of the two systems must not appreciably deviate from values set beforehand, in order to avoid an accumulation of blood in the venous system and the circulatory system of the lungs. The flow resistances of the circulatory system loops will determine how much effect is exerted during the working strokes of the pumps.

For a better understanding of the invention, reference may be made to the following description of an exemplary embodiment and variations of this embodiment, called "second" and "third" embodiments, taken in conjunction with the figures of the accompanying drawings.

DESCRIPTION OF THE EMBODIMENT

Figure 1:
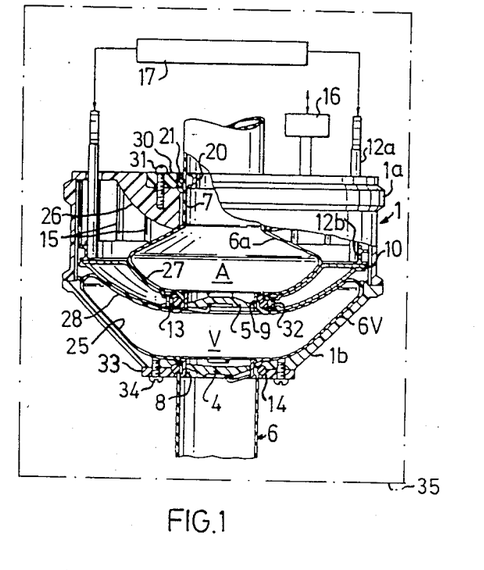
FIG. 1 is a side cross-sectional view of the embodiment taken along an axis of rotational symmetry, some of the components being shown diagrammatically.
Figure 2:
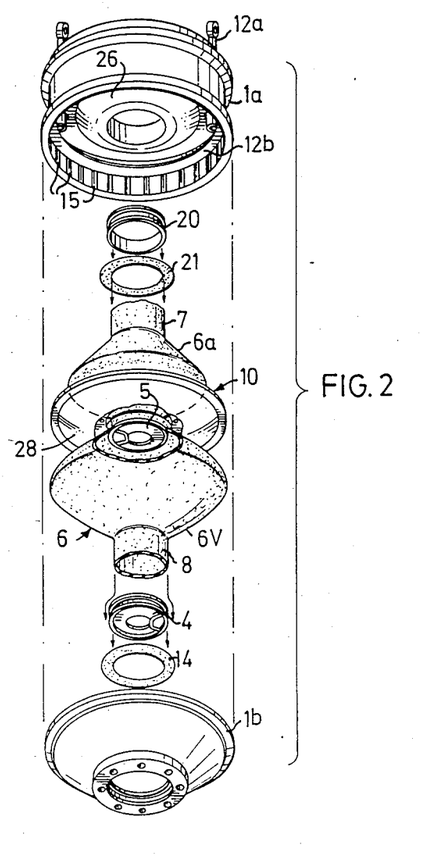
FIG. 2 is an exploded pictorial view of the embodiment.

The embodiment shown in the drawings, FIGS. 1-3, which is the best mode known to the inventor at present, is a laboratory prototype that has been built and tested. It is based on a hose-like member 6, made of a material that is flexible but substantially not extensible, mounted in a casing 1 composed of parts 1a and 1b. The member 6, whose general form, as best seen in FIG. 1, is a tube having a smaller bulb 6a and a larger bulb 6v, each of generally bell-shape, has been produced in the following way—first a paraffin form was turned on a lathe and then polished by heat input; it was coated with an elastomer, in this case silicone rubber, in several layers, with reinforcing material inlaid (gauze bandage in laboratory device), and allowed to set.

In the construction 9 between the bulbs 6a and 6v a dish-like rigid drive ring 10 is mounted (for the sake of low weight consisting of two thin sheet metal dishes fastened together and provided with holes). The drive ring is mounted in the casing 1 together with valves 4 and 5, in this case heart valves of known make, so-called Bjork-Shiley-valves. It is possible to use other valve also, e.g, those according to Sant-Jude.

As is evident from the drawings, the hose member 6 is fastened to other parts of the assembly in three places, namely to the valve 5 in the constriction 9 and also at openings 7 and 8 in the casing 1. In the case of the housing opening 7 a ring 20 with an external groove is inserted into the hose member 6 and an elastic O-ring 21 is placed on the outside. A retainer ring 30 fastened by screws 31 to the casing 1 clamps the O-ring 21 and ring 20 in place. Valves 4 and 5, besides their valve functin, also aid in fastening the hose member 6 to the drive ring 10 and the housing opening 8, respectively. Each valve has a peripheral groove that accepts an elastic O-ring, the hose member being clamped to the valve by the O-ring. The plates of the drive ring 10 are clamped to the O-ring 13 around the valve 5, and are held together, by screws 32. The O-ring 14 of the valve 4 is clamped to the housing opening 8 by a retainer ring 33 fastened to the housing by screws 34.

The whole arrangement is shown in mounted condition in FIG. 1. The drive ring 10 runs freely up and down in the rigid casing 1, which has grooves 15 on its inner surface so that air can pass freely between the sections of the casing on either side of the drive ring 10.

The smaller bulb 6a of the hose member 6 defines an atrium chamber (labelled "A") and the larger bulb 6v a ventricle chamber (labelled "V"). The inlet opening to the atrium chamber A is joined to the casing at the opening 7.

The constriction 9 between the two bulbs 6a and 6v is a passage through which blood can flow only from the atrium chamber A to the ventricle chamber V through the one-way valve 5. The opening 8 containing the one-way valve 4 is the outlet from the pump through which blood is delivered in pulses under pressure.

The volumes in the respective atrium and ventricle chambers of the pump at some stages during each cycle of operation are controlled by engagement of the bulbs 6a and 6v that define them between the lower and upper walls 25 and 26 of the casing and the lower and upper surfaces 28 and 27 of the drive ring 10. In particular, the casing surface 25 is concave (e.g., generally conical) while the surface 28 of the drive ring is convex. Similarly, the bulb 6a is engaged during a part of each cycle of the pump between a convex surface 26 of the casing and a concave surface 27 of the drive ring. In other words, each bulb is engaged between complementary, generally dishshaped, surfaces of the housing and the drive ring. It is possible for both surfaces of the drive ring to be convex surfaces, in which case the surface of the casing that engages the bulb 6a would be concave, but this is not preferred because the passage 9 between the chambers A and V would become long and introduce an undesirable pressure loss.

Figure 4:
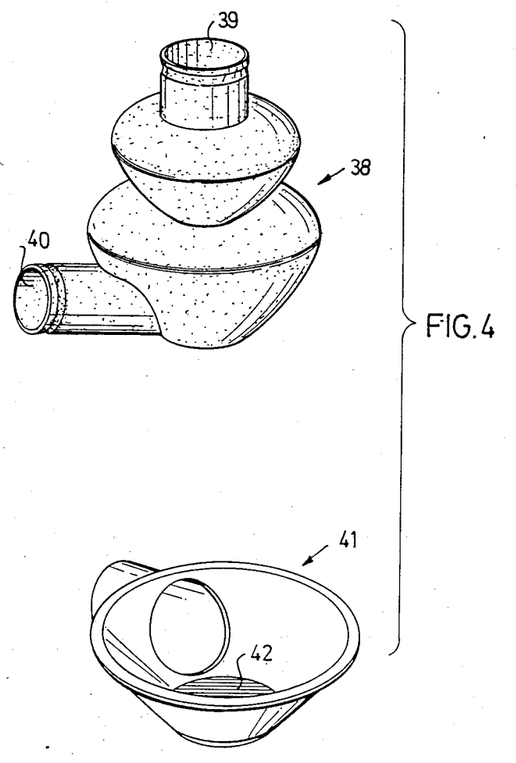
FIG. 4 is a pictorial view of part of a second embodiment.

It is also possible, but not preferred, for the hose-like member 6, the casing and the drive ring to be asymmetrical. On the other hand, it is entirely possible for the inlet and outlet portions of the hose member 6 to be located at angles oblique or perpendicular to a line (imaginary) connecting the inlet and outlet openings 7 and 8. Such a hose member 38 with inlet and outlet openings 39 and 40 is shown in FIG. 4. The lower part of the casing will have to be different in form compared with the corresponding part 1b in FIG. 2. With this type of hose member it is advantageous to arrange the drive device adjacent to the flat portion 42 of part 41.

Figure 5:
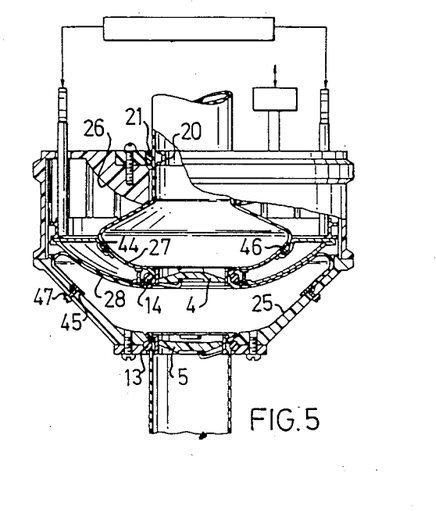
FIG. 5 is a side cross-sectional view of a third embodiment taken along an axis of rotational symmetry, some of the components being shown diagrammatically.

It also is possible to omit all or some of those portions of the flexible hose member which during the entire pumping cycle are permanently engaged with the lower and upper walls 25 and 26 of the casing and with the lower and upper surfaces 28 and 27 of drive ring 10. It is preferred to omit the portion of the flexible member 6 permanently engaging with the lower wall 25, and the portion of the flexible member 6 permanently engaging with the upper surface 28 of drive ring 10. FIG. 5 depicts a second embodiment modified accordingly. The ends of the remaining parts of the flexible hose member are secured at surfaces 27 and 25 by concentric fixtures 44 and 45 provided with a number of concentrically arranged screws 46 and 47, and at the peripheral groove in valves 4 and 5 as well as in ring 20 by squeezing through the action of O-rings, 14, 13, and 21. The omitted portions of the flexible hose member have thus been replaced by part of surfaces 25 and 27. These new surfaces have to be made in non-thrombogenic material or have to be modified in order to make them non-thrombogenic. The second embodiment is advantageous with respect to the manufacture of the flexible portions of the hose member.

The pump may be driven by any of a variety of electrical or pneumatic drive devices 17, as represented schematically in FIG. 1. The unilateral driving force is applied to the drive ring 10 in the embodiment by a push ring 12b carried by a pair of diametrically located push rods 12a that project out of the casing through openings in the top wall and are sealed by suitable sliding seals (not shown such that the casing is hermetically sealed. The push rods are acted upon through a suitable linkage by a pneumatic or electric motor. In the laboratory pump, the motor is a pneumatic cylinder having a build-in return spring. Pulses of compressed air supplied to the cylinder and acting through the linkage push the push ring 12b down into engagement with the drive ring 10 on the driven stroke of each pump cycle. At the end of the driven stroke, the push rods and push ring disengaged from the drive ring and are retracted to the top of the casing by the return spring of the pneumatic cylinder.

During each down stroke of the push ring and drive ring, the volume of the ventricle chamber is reduced, the pressure of the blood in the ventricle chamber being thereby increased, causing the valve 5 to close and the outlet valve 4 to open so that blood is pumped from the ventricle chamber. Meanwhile, the volume of the atrium chamber A increases so that blood continues to flow into the chamber during the driven stroke, i.e., the systolic phase, of the pump. At the end of the downstroke, the push ring 12b is retracted, so that pressure is no longer applied to the ventricle chamber. Nonetheless, blood will continue to flow out of the ventricle chamber through the outlet opening 8 due to the momentum imparted to the blood during the downstroke of the drive ring. The valve 5 will open when the pressure in the ventricle chamber V drops, and blood will begin to flow from the atrium chamber into the ventricle chamber. When the momentum that sustains flow through the outlet valve 4 subsides, the valve will close. The pressure of the incoming blood, together with the momentum of blood then passing from the atrium chamber to the ventricle chamber through the valve 5, will produce net upward forces exerted by the ventricle chamber bulb 6v against the bottom surface 28 of the drive ring 10, the area of engagement (normalized by projection on an imaginary plane perpendicular to the directional axis of movement of drive ring 10) between the bulb 6v and the under surface of the drive ring being greater than the area of engagement (normalized as above) between the bulb 6a and the upper surface 27 of the drive ring. Hence, the drive ring is lifted upwardly, and some of the incoming blood passes into the ventricle chamber, the volume of which is increasing as the drive ring rises. The extent of filling of the ventricle chamber on the return stroke of the pump, and therefore, the output of the pump depends upon the pressure of the incoming blood.

There is one qualification on the capability of the invention for self-regulation of the output in accordance with the pressure of the incoming blood. The qualification is that each driven stroke begins before the pump chambers reach their maximum volume. After the maximum volume is reached, no more blood can flow into the pump, the pressure of the incoming blood will rise, and a state of hypertension will be attained. Accordingly, the frequency of the drive pulses of the drive device 17 for the pump are established to ensure that the chambers of the pump do not reach maximum volume between the driven strokes. A given drive frequency can, however, accomodate the self-regulating function of the pump over a range of inflow pressures and outflow rates.

The extent to which the chambers of the pump are filled during each operating cycle of the pump is also influenced by the pressure of the gas within the casing and externally of the pump chambers. During each driven stroke of the pump, the volume occupied by the gas increases, and the pressure of the gas drops accordingly. The drop in gas pressure outside the chambers increases the net pressure difference between the incoming blood and the external gas pressure tending to resist the inflow of blood. During the return stroke of the pump, the total volume of the chambers increases, the volume of the gas in the casing decreases and the pressure of the gas in the casing increases accordingly. As the pressure in the gas approaches the pressure of the incoming blood, the rate of filling of the chambers decreases. It is apparent, therefore, that the pressure changes that occur in the gas in the casing have a regulating effect on the filling of the pump throughout each cycle. The gas pressures prevailing in the casing are determined, for one thing, by the relationship between the displacement volume of the pump and the volume occupied by the gas in the casing at any given point in the operating cycle, which is a matter of the geometric design of the pump. The amount of the gas in the casing can be regulated by a pressure control valve 16 composed of two one-way valves set to provide high and low limits on the gas pressure in the casing.

Figure 3A:
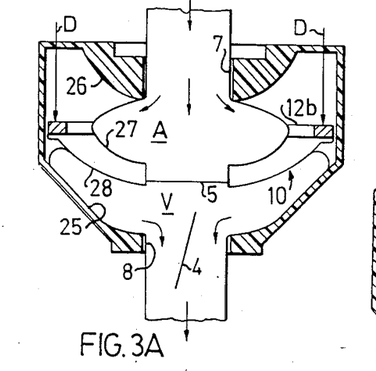
FIGS. 3A to 3D are diagrams of the embodiment at various stages of its operation.

FIGS. 3A to 3D of the drawings shows the embodiment schematically at four points in an operating cycle. FIG. 3A shows the pump at the end of the driven stroke, i.e., at the point where the push ring 12b is at the end of its downward travel under the unilateral drive force exerted on the drive ring, as represented by the arrows D. During the downstroke of the push ring, the drive ring 10 compresses a ventricle chamber V, thereby applying pressure to the blood and pumping blood from the ventricle chamber out past the open one-way valve 4 through the outlet opening 8. The pressure applied to the blood in the ventricle chamber during the driven stroke holds the valve 5 closed. The downstroke of the drive ring 10 changes the geometry of the atrium chamber A such that its volume can increase, thereby allowing blood to enter through the inlet 7 during the downstroke. The total volume of the chambers A and V decreases during the downstroke (driven stroke), thereby increasing the gas volume within the casing 1, which results in a drop in the gas pressure in the casing.

Figure 3B:
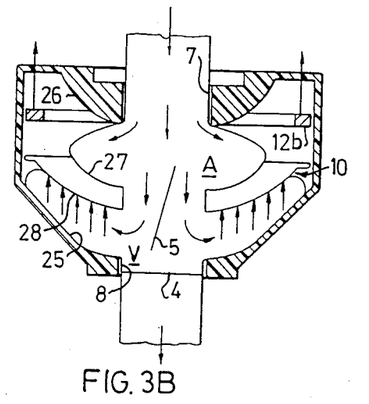

Referring to FIG. 3B, the drive device retracts the push ring 12b at the end of the driven stroke. For a short time after the retraction of the push ring, the momentum of blood flowing through the outlet 8 will keep the valve 4 open, and an additional outflow will occur. The hydrostatic pressure in the ventricle chamber will, however, drop abruptly, and the valve 5 will open due to both the hydrodynamic and hydrostatic pressures of blood entering the atrium chamber. Accordingly, a force due to pressure is exerted by the flexible walls of the ventricle chamber bulb 6V on the under surface 28 of the drive ring 10. (Of course, a similar pressure force is applied to all surfaces of the ventricle chamber.) A force due to pressure, but of lesser magnitude, will be exerted by the walls of the atrium chamber bulb 6a on the upper surface 27 of the drive ring 10, but the geometry of the bulbs and the surfaces of the drive ring engaged by the bulbs and the surfaces of the drive ring engaged by the bulbs is such that there is a net upward force due to pressure applied to the drive ring during part of the period between driven strokes which causes the drive ring to rise.

The convex surface 26 progressively affects the adjacent part of bulb 6a when drive ring 10 moves towards that surface, and the differential decrease in volume of bulb 6a approaches the differential increase in volume of bulb 6v. At a certain point both become equal. The upward movement of drive ring 10 then ceases, no matter how great the difference in pressure between chambers A and V, on the one hand, and that prevailing outside these chambers, on the other. This arrangement of surfaces affecting chambers A and V in a way that a maximum in total volume is attained before drive ring 10 has traveled to its limit in the direction towards the inlet has a protective effect on the flexible material in bulb 6 which becomes especially important in continuous use in a pump which is not hermetically sealed and is working at, e.g., atmospheric pressure. If used as a heart assist device or the like, the movement of drive ring 10 will be controlled by the static and dynamic forces of the incoming blood in interaction with the varying pressure exterioirly to chambers A and V in the hermetically sealed casing, provided that the pressure inside the casing is set in a way that does not allow the maximum total volume of chambers A and V, and therefore the point of maximum pressure inside the casing, to be reached.

Figure 3C:
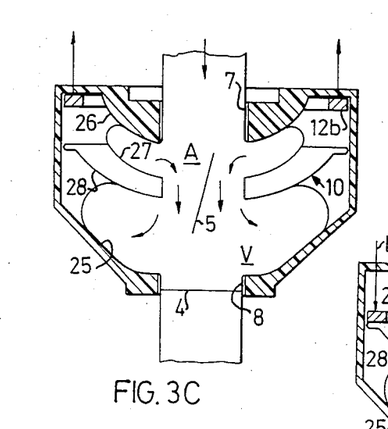

As shown in FIG. 3C, the upward force acting on the drive ring lifts it and allows the volume of the ventricle chamber to increase. The size and the geometry of the two chambers are such that even though the size of the atrium chamber decreases, the total volume of the atrium and ventricle chambers continues to increase as blood flows into the pump chambers. The effect of the pressure of the incoming blood, however, diminishes, the higher the position of the drive ring 10 and the greater the total volume of the chambers, inasmuch as the areas of the drive ring engaged by the walls of the respective chambers changes (see FIG. 3C), and the gas pressure in the space between the casing and the chamber increases. Moreover, the influence of the momentum of the incoming blood diminishes.

Figure 3D:
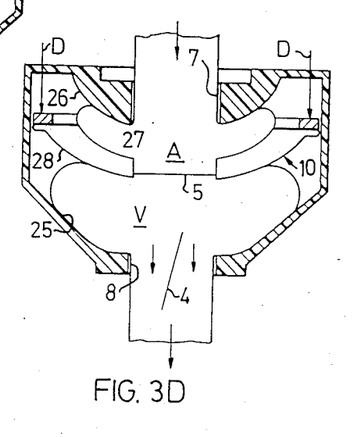

Before the drive ring rises to a position where the total volume of the chambers is at a maximum (pressure within casing constant) or, when the pressure in chamber A and V and the pressure in the room between said chambers and the hermetically sealed casing 1 have become equal (pressure within casing affected by variation of total volume of A and V in dependence of the static and dynamic forces of the incoming blood), the next driven stroke is commenced by downward movement of the push ring 12b by the force of the drive device (the arrows D), as shown in FIG. 3D. At higher stroke frequencies when dynamic forces are becoming even more important and equilibrium is no longer attained, output will be still proportional to the pressure of the incoming blood.

For in vivo application, the casing and the drive device 17 may be mounted in an enclosure, preferably a bag of, e.g., silicone rubber, of such a volume that the whole has a density of about 1 g/ccm, corresponding to the density of the body, causing the weight of the whole to correspond to the weight of the volume replaced. Such a bag is represented schematically in phantom lines in FIG. 1 designated 35. The pressure control valve 16, e.g., two one-way valves, one in each direction, provides communication between the interior and exterior of the casing 1 with predetermined opening pressures for advantageous pressure regulation.

A sensor device may be provided for monitoring the highest position of the drive ring 10 during a stroke. If the patient because of exertion, or otherwise, is consuming more blood by increased flow, this will become noticeable because the drive ring 10 rises higher, up towards the maximum volume. It is then possible to arrange a control circuit which increases the stroke frequency of the drive device, and a fully natural regulation is thus obtained.

It is most likely that the peripheral resistance is not critical for the cardiac output, but that the regulating factor at first hand is the influx. This finding is likely to change the views on cardiology in a far-reaching and decisive manner.

A laboratory pump, built according to the drawings, with an outer diameter of 90 mm, a height of the circular cylindrical part of the casing of 32 mm, and a diameter of the valves of 27 mm, gave the following results. At a constant stroke frequency of 250 beats per minute and an influx pressure corresponding to a 6 cm water column, 13.3 liter per minute were obtained. With an influx pressure of 6.5 cm water column, 15.8 liter per minute were obtained. At the outlet 350 mm Hg (systolic) and 60 mm Hg (diastolic) were obtained. Testing was done with water. The calculated displacement volume was 60 ccm for the ventricle chamber (large bulb 6v) and 28 ccm for the atrium chamber (small bulb 6a).

Thus, the invention provides a pump in which the valve plane is raised, not by its own force but because of the liquid pouring in, due to pressure of the liquid and to momentum building up during the systolic phase. Once the valve plane has moved downwards maximally and is turning back, because the liquid tends to continue unabatedly, the valve will work as a collapsible wall, the position of which moves counter to the inflow until the next drive stroke starts. The valve corresponding to the aortic valve will close when the flow through it ceases, which depending on the velocity may be later than the moment at which the valve plane inside the pump has reached the lowest position. It is even conceivable that the counterpart of the aortic valve remains open during part of the diastolic phase, which becomes shorter and shorter, the higher the frequency.

I claim:

1. A blood pump comprising an atrium chamber defined by flexible walls and having an inlet and an outlet, a ventricle chamber defined by flexible walls and having an inlet and outlet, a passage communicating the outlet of the atrium chamber with the inlet of the ventricle chamber, a first one-way valve in the passage adapted to permit blood flow only from the atrium chamber to the ventricle chamber, a second one-way valve in the outlet from the ventricle chamber adapted to permit blood to flow through the outlet only out of the ventricle chamber, a casing having first and second openings, means connecting the atrium chamber inlet to the first opening and the ventricle chamber outlet to the second opening such that the flexible walls defining the chambers are movably supported in the casing, and drive means for periodically moving the walls of the ventricle chamber to decrease the volume thereof and expel blood therefrom while simultaneously moving the walls of the atrium chamber such that its volume may increase upon inflow of blood into the inlet thereto, the drive means including a drive ring surrounding and joined to the passage and having a surface engageable with the walls of the ventricle chamber, characterized in that said surface is engageable over a selected varying area such that the pressure of blood entering the ventricle chamber betwen driven strokes of the drive means controls the output of the blood pump by establishing the magnitude of the return stroke of the drive ring as a function of a pressure force acting over the area of engagement between the drive ring and the walls of the ventricle chamber and in that the drive means engages the drive ring only during the driven stroke of the pump and disengages from the drive ring and moves to a retracted position during the return stroke of the pump, whereby the return stroke of the drive ring is provided solely by said pressure force.

2. A blood pump according to claim 1 characterized in that the casing is hermetically sealed and contains a gas exteriorly of the chambers, the pressure of which varies as a function of the variation of the instantaneous total volume of the chambers and thereby influences the inflow of blood.

3. A blood pump according to claim 2 characterized in that it comprises pressure control valve means for controlling the pressure of the gas in the casing.

4. A blood pump according to claim 3 characterized in that it comprises an enclosure containing the casing and all components of the drive means and pressure control valve means communicating the interior of the casing with the enclosure.

5. A blood pump according to claim 1 characterized in that the atrium and ventricle chambers and the passage are portions of a one-piece hose-like member of flexible and substantially non-extensible material.

6. A blood pump according to claim 1 characterized in that the inlet to the atrium chamber and the outlet from the ventricle chamber are at generally opposite ends of the casing and are also generally opposite the passage across the respective chambers.

7. A blood pump according to claim 6 characterized in that the chambers and passage are substantially symmetrical rotationally about an axis of symmetry defined by a line joining the inlet to the atrium chamber and the outlet from the ventricle chamber.

8. A blood pump according to claim 7 characterized in that the casing and the drive ring are substantially symmetrical rotationally about an axis of symmetry coincident with the axis of symmetry of the chambers and passage.

9. A blood pump according to claim 1 characterized in that the inlet passage, the atrium chamber, the passage between the atrium and ventricle chambers, and the part of the ventricle chamber which is bordering to the passage between the atrium and ventricle chambers and which during a complete operating cycle does not permanently remain engaged with an interior wall surface are substantially rotationally symmetrical about an axis defined by a line joining the inlet to the atrium chamber and the passage between the atrium chamber and the ventricle chamber, and wherein the outlet from the ventricle chamber is located at an angle oblique or perpendicular to said axis.

10. A blood pump according to claim 9 characterized in that the drive device is arranged adjacent to the portion of the ventricle chamber bordering to the casing.

11. A blood pump according to claim 1 characterized in that portions of the walls of each chamber are engageable during portions of each operating cycle between a surface of the drive ring and an interior wall surface of the casing, and wherein the surfaces engageable with the respective chamber walls are dish-shaped and of generally complementary shapes.

12. A blood pump according to claim 11 characterized in that the surface of the drive ring that engages one of the chambers is convex and the surface of the drive ring that engages the other chamber is concave.

13. A blood pump according to claim 11 characterized in that the area of the surface of the drive ring that engages the ventricle chamber is substantially greater than the area of the surface of the drive ring that engages the atrium chamber during a substantial part of the return stroke of the pump, whereby the volume of blood taken into the pump between driven strokes is a function of the pressure of the blood entering the chambers during the return stroke.

14. A blood pump according to claim 11, characterized in that the portions of the walls of each chamber, which during a complete operating cycle remain engaged with a surface of the driving ring or an interior wall surface of the casing, are completely or partially replaced by said surfaces of the driving ring or of the casing interior wall.

15. A blood pump according to claim 14 characterized in that the portions of the walls of the atrium and ventricle chamber to be replaced are preferentially the portion of the atrium chamber engaged with the surface of the drive ring, or the portion of the ventricle chamber engaged with the wall of the casing, or both.

16. A blood pump according to claim 12 characterized in that the convex portion of the interior wall surface of the casing engaging with part of the atrial chamber wall is made to substantially affect the volume of said atrium chamber between driven strokes in a way that a maximum in the total volume of the atrium and ventricle chambers ensues substantially before the drive ring reaches its mechanical limit of movement in the direction of the atrial chamber.

* * * * *